US012775015B2

(12) United States Patent
Daniels et al.

(10) Patent No.: US 12,775,015 B2
(45) Date of Patent: Oct. 27, 2026

(54) PHENACYLBROMIDE-BASED MASS TAGS FOR CARBOXYL AND PHENOLIC FUNCTIONAL GROUP CONTAINING ANALYTES

(71) Applicant: DH Technologies Development Pte. Ltd., Singapore (SG)

(72) Inventors: Scott Daniels, Concord (CA); Subhakar Dey, Lexington, MA (US); Subhasish Purkayastha, Concord (CA)

(73) Assignee: DH Technologies Development Pte. Ltd., Singapore (SG)

( * ) Notice: Subject to any disclaimer, the term of this patent is extended or adjusted under 35 U.S.C. 154(b) by 793 days.

(21) Appl. No.: 18/020,690

(22) PCT Filed: Aug. 11, 2021

(86) PCT No.: PCT/IB2021/057423
§ 371 (c)(1),
(2) Date: Feb. 10, 2023

(87) PCT Pub. No.: WO2022/034528
PCT Pub. Date: Feb. 17, 2022

(65) Prior Publication Data

US 2023/0258652 A1 Aug. 17, 2023

Related U.S. Application Data

(60) Provisional application No. 63/064,710, filed on Aug. 12, 2020.

(51) Int. Cl.
*G01N 33/68* (2006.01)
*G01N 33/58* (2006.01)
*G01N 33/74* (2006.01)

(52) U.S. Cl.
CPC ......... *G01N 33/6848* (2013.01); *G01N 33/58* (2013.01); *G01N 33/743* (2013.01); *G01N 2458/15* (2013.01); *G01N 2560/00* (2013.01)

(58) Field of Classification Search
CPC .. G01N 33/6848; G01N 33/58; G01N 33/743; G01N 2458/15; G01N 2560/00; G01N 33/92
See application file for complete search history.

(56) References Cited

U.S. PATENT DOCUMENTS

2004/0254177 A1* 12/2004 Amici .................... A61P 13/08 514/254.06

FOREIGN PATENT DOCUMENTS

JP 2005331465 A 12/2005
WO 2016115249 A1 7/2016

OTHER PUBLICATIONS

Watkins. Fluorescent/Ultraviolet Absorbing Ester Derivative Formation and Analysis of Eicosanoids by High-Pressure Liquid Chromatography. 1982. Analytical Biochemistry. (Year: 1982).*

(Continued)

*Primary Examiner* — Rebecca M Fritchman
(74) *Attorney, Agent, or Firm* — Potomac Law Group, PLLC; Reza Mollaaghababa; Michael J. Bastian

(57) ABSTRACT

A derivatizing reagent, set of derivatizing reagents, and derivatizing techniques are provided herein for the relative quantitation, absolute quantitation, or both, of analytes containing carboxyl and/or phenolic functional groups including those analytes that may be difficult to analyze via mass spectrometry using traditional techniques of ionization. By way of non-limiting examples, such analytes can include fatty acids, carnitines, eicosanoids, and estrogens. Methods for producing the derivatizing reagent are also disclosed.

10 Claims, 8 Drawing Sheets

Phenolic Estradiol PAB-Based Agent Derivatized Phenolic Estradiol

(56) References Cited

OTHER PUBLICATIONS

Chhonker. Quantification of eicosanoids and their metabolites in biological matrices: a review. 2018. Bioanalysis. (Year: 2018).*
Choo in WO 2016111538. Machine translation. 2016. (Year: 2016).*
Huang. Formation and determination of the oxidation products of 5-methylcytosine in RNA. 2016. (Year: 2016).*
International Search Report for PCT/IB2021/057423 mailed Oct. 29, 2021.
Willacey Cornelius C W et al., "LC-MS/MS analysis of the central energy and carbon metabolites in biological samples following derivatization by dimethylaminophenacyl bromide", Journal of Chromatography A, Elsevier, Jul. 13, 2019, vol. 1608.
Written Opinion for PCT/IB2021/057423 mailed Oct. 29, 2021.

* cited by examiner

Sample = 10 mM Arachidonic Acid (unlabeled)

Sample = 50 µM Derivatized Arachidonic Acid

Phenol

PAB-Based Agent

Derivatized Phenol

Phenolic Estradiol

PAB-Based Agent

Derivatized Phenolic Estradiol

● = $^{13}$C enriched center

PHENACYLBROMIDE-BASED MASS TAGS FOR CARBOXYL AND PHENOLIC FUNCTIONAL GROUP CONTAINING ANALYTES

RELATED US APPLICATIONS

This application is a 35 U.S.C. 371 national stage filing of International Application No. PCT/IB2021/057423 filed on Aug. 11, 2021 which claims the benefit of priority from U.S. Provisional Application No. 63/064,710, filed on Aug. 12, 2020, entitled "Phenacylbromide-Based Mass Tags for Carboxyl and Phenolic Functional Group Containing Analytes," the entire contents of which is hereby incorporated by reference.

FIELD

The present teachings generally relate to mass spectrometry, and more particularly to tagging reagents useful for mass spectrometry.

INTRODUCTION

Mass spectrometry (MS) is an analytical technique for determining the elemental composition of test substances with both qualitative and quantitative applications. MS can be useful for identifying unknown compounds, determining the isotopic composition of elements in a molecule, determining the structure of a particular compound by observing its fragmentation, and quantifying the amount of a particular compound in a sample. Given its sensitivity and selectivity, MS is particularly important in life science applications.

The accurate analysis and quantitation of acid-containing compounds containing terminal carboxyl groups is becoming increasingly important. For example, the quantity of acid-containing compounds (e.g., fatty acids and eicosanoids) in physiological samples can provide diagnostic information for various disease states. Likewise, the analysis of compounds containing phenolic OH groups (e.g., hormones) is clinically critical. For example, the quantitation of estrogen and estrogen-like compounds helps in the management of estrogen related diseases (e.g., breast cancer).

Because mass spectrometers detect chemical entities as ions, a conversion of a compounds to be analyzed to charged ions must occur during sample processing. However, mass spectrometric analysis of these carboxyl and phenolic functional group containing compounds has presented challenges due to the compounds' low ionization efficiency, for example, because many of these compounds do not contain ionizable groups. As a result, quantitation of such analytes within a sample, and especially when at low concentrations within a sample comprising a biological matrix, can be difficult.

A need therefore exists for improved techniques for quantitating such analytes containing carboxyl or phenolic functional groups that overcome these drawbacks.

SUMMARY

Various aspects of the present teachings provide a labeling reagent, a set of labeling reagents, and labeling techniques for the analysis (e.g., relative quantitation, absolute quantitation, or both) of analytes containing carboxyl or phenolic functional groups. Such analytes may be difficult to analyze via mass spectrometry using traditional techniques of ionization, and may include, for example, fatty acids, bile acids, carnitines, eicosanoids, and estrogens (e.g., estrone, estradiol, estriol) that are useful in the diagnosis for various disease states. Methods for producing the labeling reagent are also disclosed as well as methods for their use in mass spectrometry.

In accordance with various aspects of the present teachings, a method of analyzing a sample is provided, the method comprising reacting a sample containing or suspected of containing one or more analytes having at least one of a carboxyl and a phenolic functional group with a derivatizing agent to produce one or more derivatized analytes, wherein the derivatizing agent comprises a substituted or non-substituted phenacyl bromide (PAB) and derivatives thereof. The method further comprises analyzing the one or more derivatized analytes.

In some aspects, the sample contains or is suspected of containing one or more analytes having at least one carboxyl functional group. For example, in some aspects, the one or more analytes having at least one carboxyl functional group may comprise one or more of fatty acids, bile acids, amino acids, and carnitines. By way of another example, the one or more analytes having at least one carboxyl functional group may comprise at least one eicosanoid. In some related aspects, the at least one eicosanoid may comprise one or more of prostaglandin, thromboxane, EpETE (epoxyeicosatetraenoic acid), HETE (hydroxyeicosatetraenoic acid), HODE (hydroxyoctadecadienoic acid), and HpETE (hydroperoxyeicosatetraenoic acid).

In some aspects, the sample contains or is suspected of containing one or more analytes having at least one phenolic functional group. For example, in some aspects, the one or more analytes having at least one phenolic functional group may comprise at least one hormone. In various aspects, the hormone(s) may be one or more estrogens. By way of example, the one or more estrogens may be selected from the group consisting of estrone, estradiol, and estriol.

In various aspects, the sample may be a biological sample. By way of example, the biological sample may be one of blood, plasma, serum, urine, saliva, cerebral fluid, tissue, hair, or body fluids.

According to various embodiments, the derivatizing agent may be of the formula:

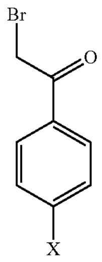

or a heavy atom derivative thereof, wherein X is hydrogen or a pyrrolidine group. For example, in certain aspects, the derivatizing agent may be a non-substituted PAB of the formula:

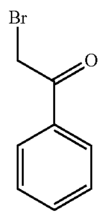

or a heavy atom derivative thereof. In some alternative aspects, the derivatizing agent may comprise a substituted PAB of the formula:

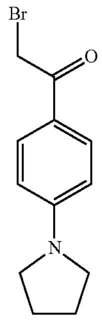

or a heavy atom derivative thereof.

According to various embodiments, the derivatizing agent may be of the formula:

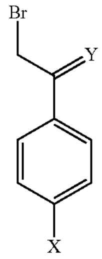

wherein X is hydrogen or a pyrrolidine group, and wherein Y is oxygen or NO—$(CH_2)_n$—$(NR_3)^+$ or a heavy atom derivative thereof, n is 1 to 20, and each R is independently hydrogen or a cyclic, branched or straight chain $C_1$-$C_{18}$ alkyl, $C_1$-$C_{18}$ alkene, or $C_1$-$C_{18}$ alkyne. For example, in certain aspects, the derivatizing agent may be of the formula:

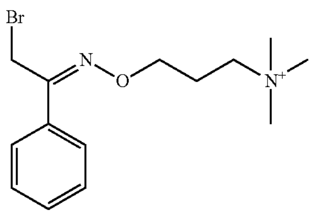 [SMILES: C[N+](C)(C)CCCO/N=C(/CBr)c1ccccc1]

or a heavy atom derivative thereof. In some alternative aspects, the derivatizing agent is of the formula:

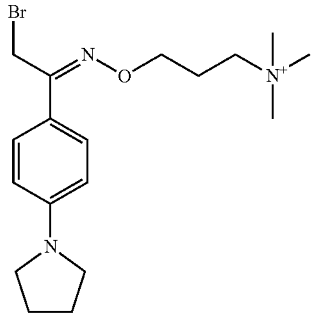 [SMILES: C[N+](C)(C)CCCO/N=C(/CBr)c1ccc(N2CCCC2)cc1]

or a heavy atom derivative thereof.

The derivatized analytes can be analyzed in a variety of manners. For example, in various aspects, analysis of the derivatized analytes may be performed by a mass spectrometer. In some aspects, for example, the derivatized analytes may be ionized in positive ion mode prior to using the mass spectrometer.

As noted above, method for producing the labeling reagent are also disclosed as well as methods for their use in mass spectrometry.

Methods for producing various derivatizing agents disclosed herein are also described herein. For example, various embodiments of methods in accordance with the present teachings comprise reacting a substituted or non-substituted phenacyl bromide with an aminooxy compound having a quaternary amine to form a derivatizing agent. In some aspects, for example, the aminooxy compound may be of the formula $H_2NO$—$(CH_2)_n$—$(NR_3)^+$ or a heavy atom derivative thereof, where n is 1 to 20, and each R is independently hydrogen or a cyclic, branched or straight chain $C_1$-$C_{18}$ alkyl, $C_1$-$C_{18}$ alkene, or $C_1$-$C_{18}$ alkyne.

In accordance with various aspects of the present teachings, a composition is provided, the composition comprising the reaction product of a substituted or non-substituted phenacyl bromide with an aminooxy compound having a quaternary amine. For example, the aminooxy compound may be of the formula $H_2NO$—$(CH_2)_n$—$(NR_3)^+$ or a heavy atom derivative thereof, where n is 1 to 20, and each R is independently hydrogen or a cyclic, branched or straight chain $C_1$-$C_{18}$ alkyl, $C_1$-$C_{18}$ alkene, or $C_1$-$C_{18}$ alkyne. By way of example, in various aspects, the composition may be of the formula:

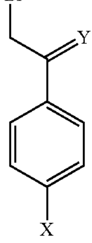

wherein X is hydrogen or a pyrrolidine group, and wherein Y is NO—$(CH_2)_3$—$(NH_3)^+$ or a heavy atom derivative thereof.

The present teachings also provides kits for mass spectrometer analysis of one or more analytes having at least one of a carboxyl and a phenolic functional group. In some example embodiments, the kit may comprise the reaction product of a substituted or non-substituted phenacyl bromide with an aminooxy compound having a quaternary amine. By way of non-limiting example, the kit may comprise a composition of the formula:

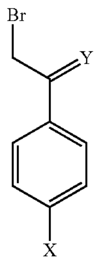

wherein X is hydrogen or a pyrrolidine group, and wherein Y is oxygen or NO—$(CH_2)_n$—$(NR_3)^+$ or a heavy atom derivative thereof, n is 1 to 20, and each R is independently hydrogen or a cyclic, branched or straight chain $C_1$-$C_{18}$ alkyl, $C_1$-$C_{18}$ alkene, or $C_1$-$C_{18}$ alkyne.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

Figure 1:
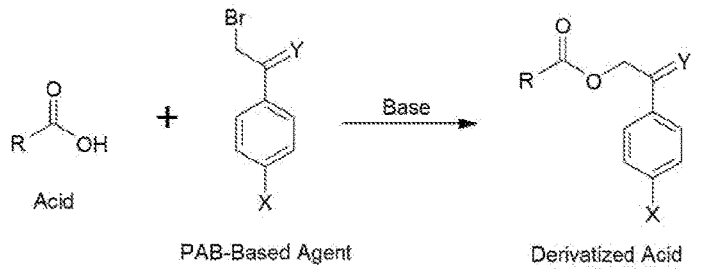
FIG. 1 depicts an exemplary reaction of an acid containing a carboxyl group with a PAB-based derivatizing agent in accordance with various aspects of the applicant's teachings.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

According to some embodiments, methods of detecting the presence of, and/or quantifying one or more analytes having at least one carboxyl or phenolic functional group in a sample are provided.

Carboxyl-containing analytes contain a carboxyl group:

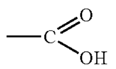

In some embodiments, a carboxyl-containing analyte can be neutral. In some embodiments, the carboxyl-containing analyte is an ion. In certain embodiments, a carboxyl-containing analyte can have a molecular weight in the range of about 50-1000 g/mol. In some embodiments, the carboxyl-containing analyte can have a molecular weight in the range of about 100-400 g/mol. In some embodiments, the carboxyl-containing analyte has 2, 3, or more carboxyl —(C(═O)OH) moieties.

Examples of analytes containing a carboxyl functional group include, but are not limited to, fatty acids, bile acids, amino acids, carnitines, and eicosanoids. Non-limiting examples of each of these classes of carboxyl-containing compounds that may be analyzed in accordance with the present teachings are shown below in Table 1:

TABLE 1
| Example analytes having at least one carboxyl functional group | | |
|---|---|---|
| Fatty Acids | 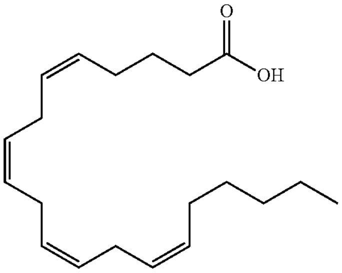 arachidonic acid | 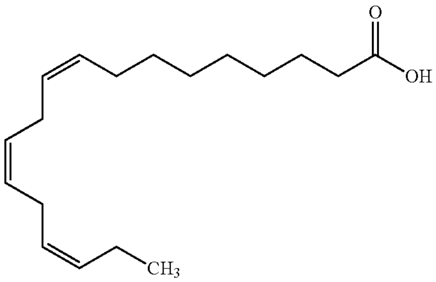 α-linolenic acid |
| Bile Acids | 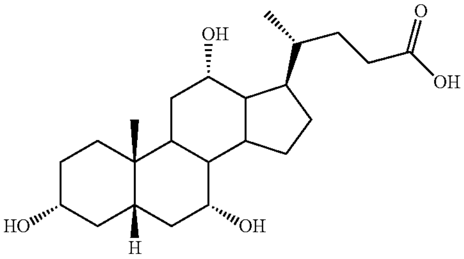 cholic acid (primary | 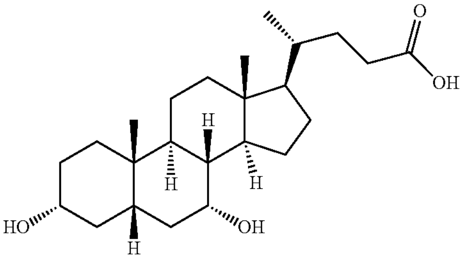 chenodeoxycholic acid (primary) |
| | 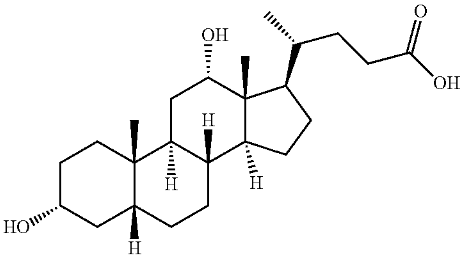 deoxycholic acid (secondary) | |
| Amino Acids | 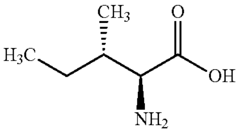 L-isoleucine | 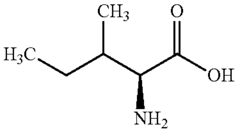 valine |
| Carnitines | 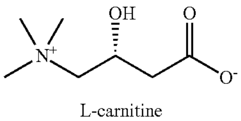 L-carnitine | 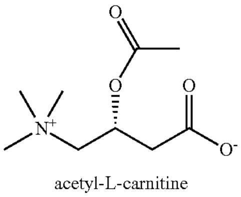 acetyl-L-carnitine |
| | 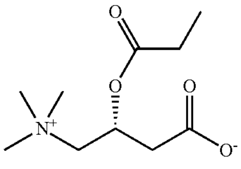 propionyl-L-carnitine | |

TABLE 1-continued

| Example analytes having at least one carboxyl functional group | |
|---|---|
| Eicosanoids | 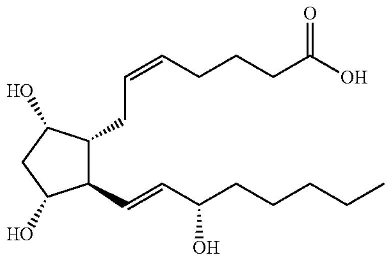 prostaglandin F2a 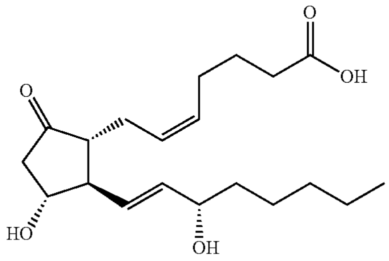 prostaglandin E2 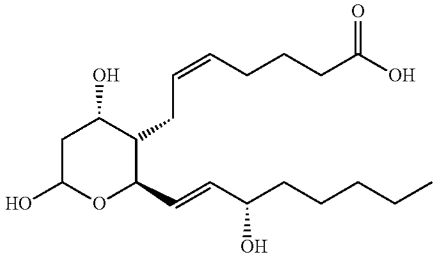 thromboxane B2 |

Generally, fatty acids are carboxylic acids with an aliphatic chain and are important structural components for cells. By way of further non-limiting example, fatty acid analytes containing a carboxyl functional group can comprise short-chain fatty acids (e.g., formic acid, acetic acid, propionic acid), medium chain fatty acids (e.g., caproic acid, caprylic acid, capric acid), long chain fatty acids (e.g., palmitic acid, stearic acid, arachidic acid), very long chain fatty acids (e.g., docosanoic acid, tetracosanoic acid, and hexacosanoic acid), branched chain fatty acids (e.g., phytanic acid, pristanic acid), saturated fatty acids (propanoic acid, butyric acid, valeric acid), monounsaturated fatty acids (e.g., myristoleic acid, palmitoleic acid, vassenic acid), and polyunsaturated fatty acids (e.g., linolenic acid, eicosapentaenoic acid, docosahexaenoic acid).

Generally, bile acids are steroid acids that are commonly synthesized in the liver (primary bile acids) or can result from bacterial action in the colon (secondary bile acids). By way of further example, according to various embodiments, the bile acids containing a carboxyl functional group can comprise primary bile acids (e.g., cholic acid, chenodeoxycholic acid) and secondary bile acids (e.g., deoxycholic acid, lithocholic acid).

Generally, amino acids contain both an amine and a carboxyl function group and have extensive biologic functions as the building blocks of proteins, as neurotransmitters, and in biosynthesis. By way of further example, according to various embodiments, amino acids containing a carboxyl functional group can comprise the standard amino acids (e.g., lysine, asparagine, threonine, etc.) and stereoisomers thereof, as well as derivatives of such amino acid such as phosphoserine (PSER), arginosuccinic acid (ASA), hydroxyproline and carnitines (e.g., D- and L-carnitines, which can be derived from lysine).

Generally, eicosanoids are metabolism products of polyunsaturated fatty acid precursors such as arachidonic acid, adrenic acid, eicosapentaenoic acid, dihomo-gamma-linolenic acid, and mead acid. Additional non-limiting examples of eiconasoids to those examples depicted above include EpETE, HETE. HODE, and HpETE.

Phenolic-containing analytes contain a phenol group:

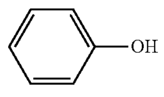

In some embodiments, a phenolic-containing analyte can be neutral. In some embodiments, the phenolic-containing analyte is an ion. In certain embodiments, a phenolic-containing analyte can have a molecular weight in the range of about 50-1000 g/mol. In some embodiments, the phenolic-containing analyte can have a molecular weight in the range of about 100-400 g/mol. In some embodiments, the phenolic-containing analyte has 2, 3, or more phenolic OH moieties.

Examples of analytes containing a phenolic functional group that may be analyzed in accordance with the present teachings include, but are not limited to, hormones, examples of which are shown below in Table 2:

TABLE 2

| Example analytes having at least one phenolic functional group | | |
|---|---|---|
| Hormones | 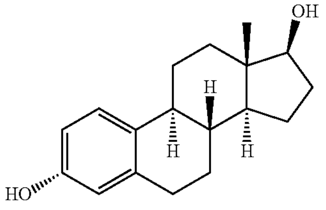<br>estradiol | 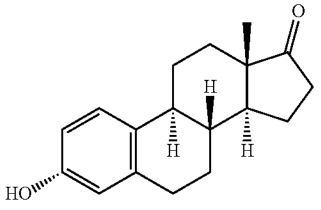<br>estrone |
| | 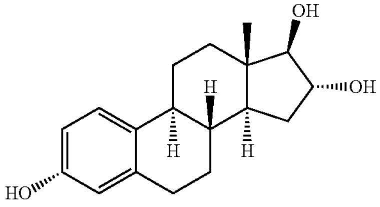<br>estriol | |

By way of further example, according to various embodiments, the analytes containing a phenolic functional group can comprise one or more steroids, steroid-like compounds, estrogen, estrogen-like compounds, estrone (E1), estradiol (E2), 17α-estradiol, 1713-estradiol, estriol (E3), 16-epiestriol, 17-epiestriol, and 16,17-epiestriol, and/or metabolites thereof. In various embodiments, the metabolites can be, for example, estriol, 16-epiestriol (16-epiE3), 17-epiestriol (17-epiE3), 16,17-epiestriol (16,17-epiE3), 16-ketoestradiol (16-ketoE2), 16α-hydroxyestrone (16α-OHE1), 2-methoxyestrone (2-MeOE1), 4-methoxyestrone (4-MeOE1), 2-hydroxyestrone-3-methyl ether (3-MeOE1), 2-methoxyestradiol (2-MeOE2), 4-methoxyestradiol (4-MeOE2), 2-hydroxyestrone (20HE1), 4-hydroxyestrone (4-OHE1), 2-hydroxyestradiol (2-OHE2), estrone (E1), estrone sulfate (E1s), 17α-estradiol (E2a), 17β-estradiol (E2b), estradiol sulfate (E2s), equilin (EQ), 17α-dihydroequilin (EQa), 17β-dihydroequilin (EQb), Eqilenin (EN), 17α-dihydroequilenin (ENa) 17β-dihydroequilenin (ENb), Δ8,9-dehydroestrone (dE1), Δ8,9-dehydroestrone sulfate (dE1s). In some embodiments, the phenol-containing analyte can be a steroid or a steroid-like compound having an A-ring which is $sp^2$ hybridized and an OH group at the 3-position of the A-ring.

In various embodiments, methods in accordance with the present teachings comprise reacting one or more analytes of interest having a carboxyl or phenolic functional group with a phenacyl bromide-based (PAB-based) derivatizing agent under conditions sufficient to derivatize the analyte(s) of interest, if any, present in the sample. Thereafter, the derivatized analyte(s) can be analyzed (e.g., detected, quantified), as discussed otherwise herein.

PAB-based derivatizing agents in accordance with the present teachings generally comprise a substituted or non-substituted phenacyl bromide (PAB) and derivatives thereof (e.g., a heavy atom derivative of non-substituted PAB or substituted PAB). Non-substituted PAB (CAS No. 70-11-1) is a compound having the following Formula I:

(I)

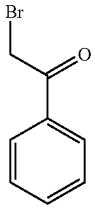

In various embodiments, a non-substituted PAB-based derivatizing agent of Formula I may be a heavy atom derivative of PAB. As used herein, the term “heavy atom” refers to an isotope of an element having an identical number of protons and electrons as the isotope of greatest natural abundance, but having at least one additional neutron, thereby increasing the molecular weight of the element by one or more mass units. Thus, as used herein, when the term “heavy atom derivative thereof” refers to a compound, the term means that one or more of the elements of the compound is replaced by a heavy atom isotope of the element. For example, in a heavy atom derivative of the PAB of Formula I, one or more of the hydrogen atoms can be deuterium, one or more of the $^{12}C$ carbon atoms can be $^{13}C$, and/or the $^{16}O$ oxygen atom can be $^{17}O$ or $^{18}O$. Similarly, a heavy atom derivative of a nitrogen containing compound can replace one or more $^{14}N$ nitrogen atoms with the heavier $^{15}N$.

In addition to PAB and heavy atom derivatives thereof, PAB-based derivatizing agents in accordance with the present teachings may additionally be substituted at one or more positions of the PAB. By way of example, PAB-based derivatizing agents in accordance with the present teachings may generally have the structure of Formula II (including heavy atom derivatives thereof):

(II)

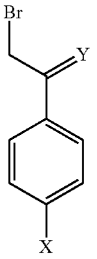

where X is hydrogen or a pyrrolidine group, and Y is oxygen or NO—$(CH_2)_n$—$(NR_3)^+$, n is 1 to 20, and each R is independently hydrogen or a cyclic, branched or straight chain $C_1$-$C_{18}$ alkyl, $C_1$-$C_{18}$ alkene, or $C_1$-$C_{18}$ alkyne.

It will be appreciated that where X is hydrogen and Y is oxygen, Formula II above represents non-substituted PAB. Thus, in various embodiments, the PAB-derivatizing agent may be PAB having no substitutions (i.e., X=hydrogen, Y=oxygen in Formula II above), a substitution only at X (e.g., X=pyrrolidine group, Y=oxygen as in Formula III below), a substitution at Y (e.g., X=hydrogen, Y═NO—$(CH_2)_n$—$(NR_3)^+$ as in Formula IV below), or a substitution at both X and Y (e.g., X=pyrrolidine group, Y═NO—$(CH_2)_n$ —$(NR_3)^+$ as in Formula V below), as well as heavy atom derivatives thereof.

(III)

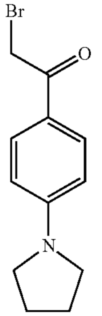 [SMILES: O=C(CBr)c1ccc(N2CCCC2)cc1]

(IV)

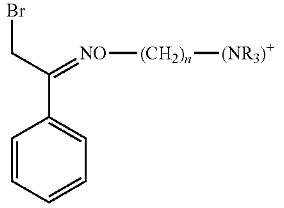

(V)

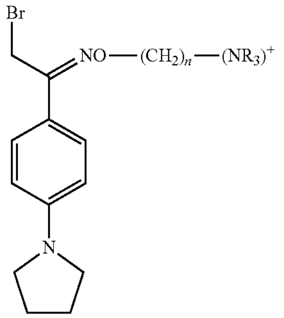

As noted above, the substitution at Y of Formula II may be NO—$(CH_2)_n$—$(NR_3)^+$ or a heavy atom derivative thereof, where n is 1 to 20, and each R is independently hydrogen or a cyclic, branched or straight chain $C_1$-$C_{18}$ alkyl, $C_1$-$C_{18}$ alkene, or $C_1$-$C_{18}$ alkyne. In some particular example embodiments, n is 3 and each R is hydrogen such that the PAB-based derivatizing agent of Formulas IV and V have the structure of Formulas VI and VII (and heavy atom derivatives thereof), respectively:

(VI)

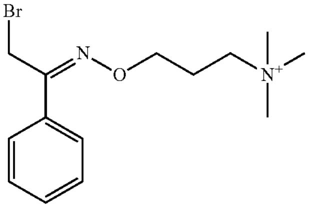

(VII)

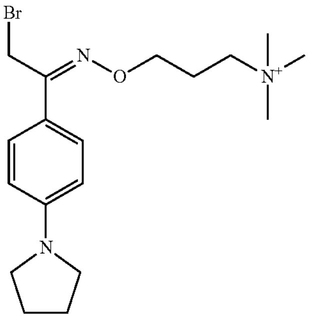

Methods in accordance with the present teachings can comprise reacting one or more analytes of interest having a carboxyl or phenolic functional group with a PAB-based derivatizing agent under conditions sufficient to derivatize the analyte(s) of interest present in the sample. FIG. 1 depicts an exemplary reaction of an acid containing a carboxyl group with a PAB-based derivatizing agent of Formula II above in the presence of a base. As shown in the exemplary reaction, the bromine of the PAB-based derivatizing agent functions as a leaving group, thereby resulting in the derivatized acid.

Figure 2A:
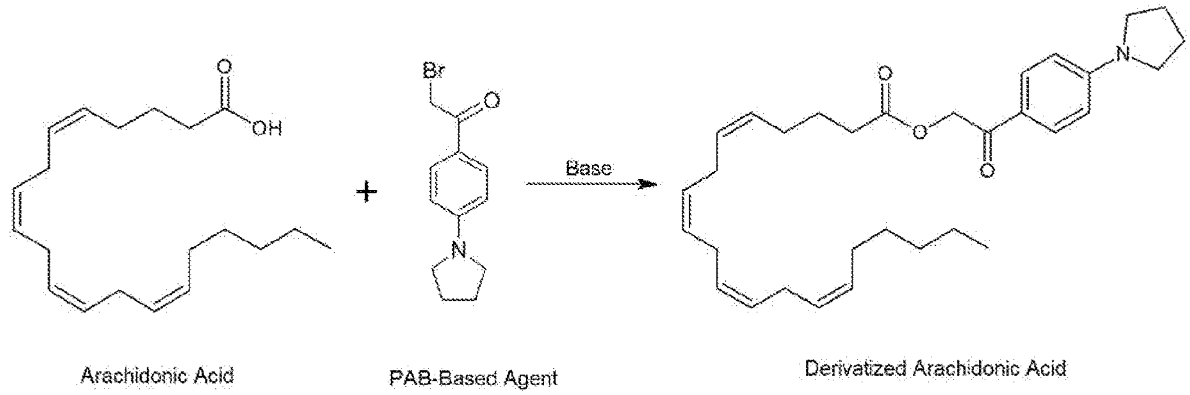
FIG. 2A depicts a reaction of arachidonic acid with an example embodiment of PAB-based derivatizing agent in accordance with various aspects of the applicant's teachings.
Figure 2B:
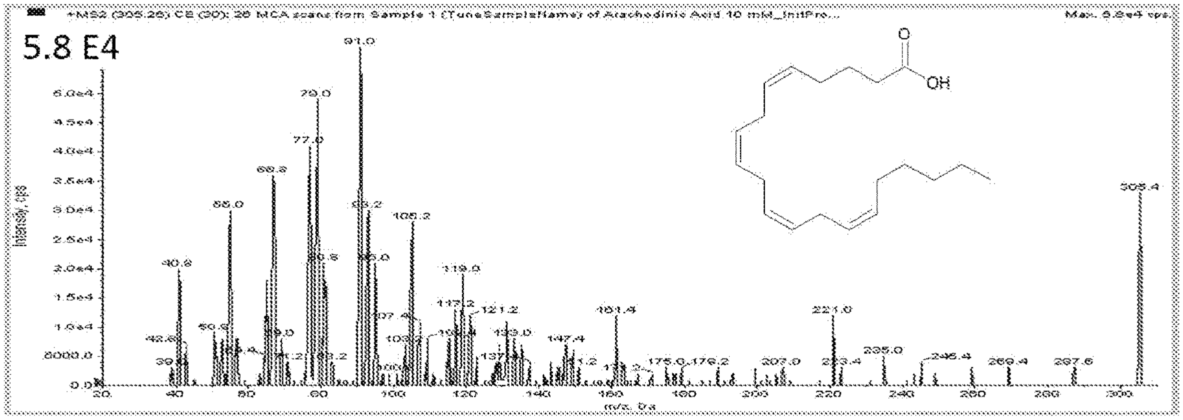
FIG. 2B depicts the mass spectra of a sample containing unlabeled arachidonic acid.
Figure 2C:
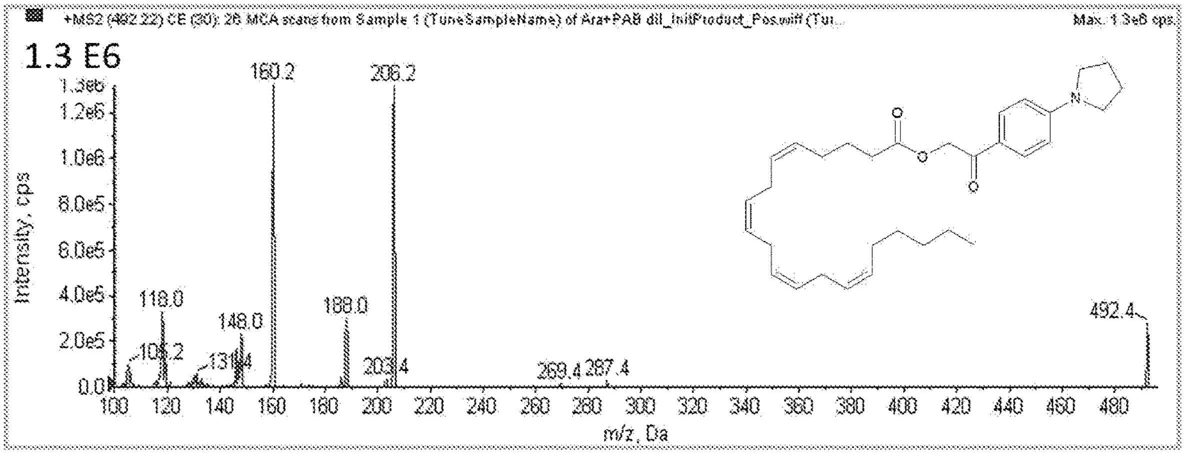
FIG. 2C depicts the mass spectra of arachidonic acid derivatized with the PAB-based derivatizing agent shown in FIG. 2A.

As a particular example of the reaction of FIG. 1, FIG. 2A depicts the reaction of the PAB-based derivatizing agent of Formula III with arachidonic acid, which is a polyunsaturated fatty acid (PUFA) that is involved in cellular signaling. As will be appreciated by a person skilled in the art, arachidonic acid is also a precursor to a wide range of eicosanoids and metabolites thereof that are biologically and clinically relevant. FIG. 2B depicts the $MS^2$ spectra of a sample containing 10 millimolar (mM) of unlabeled arachidonic acid. FIG. 2C, on the other hand, depicts the $MS^2$ spectra of a sample containing 50 micromolar (μM) of arachidonic acid derivatized with the PAB-based derivatizing agent as shown in FIG. 2A in accordance with various aspects of the present teachings. In particular, arachidonic acid was reacted with the PAB-based derivatizing agent of Formula III in 0.75 M triethanolamine in acetonitrile and heated at 60° C. for 1 h. The solutions were infused into a SCIEX 3200 QTRAP with a Turbo Spray source and the fragmentation of the product ion peak is shown. The ionization and MS conditions for FIG. 2C were identical to those used to generate the $MS^2$ spectra of FIG. 2B. Notably, despite the 200-fold greater concentration of unlabeled arachidonic acid in the sample of FIG. 2B relative to the concentration of derivatized arachidonic acid in the sample of FIG. 2C, the $MS^2$ analysis of the derivatized sample exhibited more than a 20× increase in detected maximum intensity ($1.3\times10^6$ cps vs. $5.8\times10^4$ cps), thereby demonstrating the substantially increased sensitivity resulting from PAB-based derivatization of the carboxyl-containing PUFA in accordance with various aspects of the present teachings. Without being bound by any particular theory, it is believed that this substantial increase in $MS^2$ signal resulted from the improved ionization efficiency of the derivatized analyte relative to that of the negatively-charged, unlabeled arachidonic acid. The fragmentation of underivatized arachidonic acid produces many peaks in the mass spectrum of FIG. 2B resulting in an overall dilution of the signal, whereas only a few high intensity peaks are produced with the derivatized arachidonic acid as shown in FIG. 2C.

Figure 3:
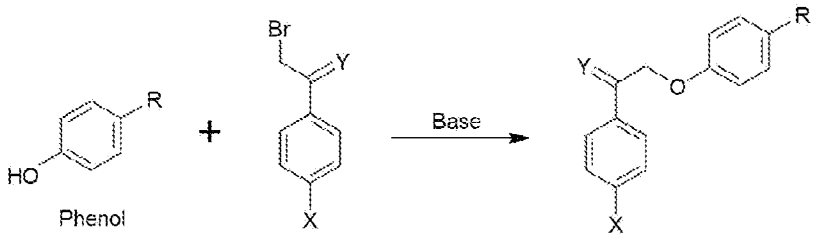
FIG. 3 depicts an exemplary reaction of an analyte containing a phenol group with a PAB-based derivatizing agent in accordance with various aspects of the applicant's teachings.
Figure 4:
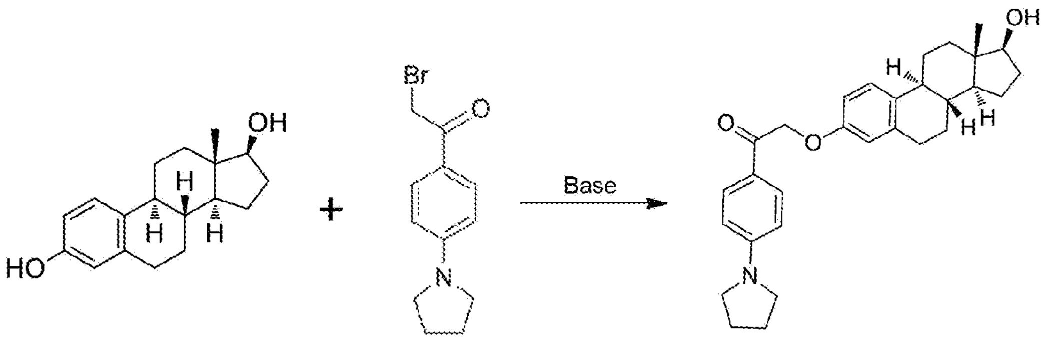
FIG. 4 depicts a reaction of estradiol with an example embodiment of a PAB-based derivatizing agent in accordance with various aspects of the applicant's teachings.

With reference now to FIG. 3, an exemplary reaction of a phenol-containing compound with the PAB-based derivatizing agent of Formula II is depicted. As shown, the bromine of the PAB-based derivatizing agent again functions as the leaving group when reacted the phenol-containing compound in the presence of a base, thereby forming the derivatized phenol. As a particular example of the reaction of FIG. 3, FIG. 4 depicts the reaction of the PAB-based derivatizing agent of Formula III with estradiol.

The analyte or analytes having at least one carboxyl or phenolic functional group can be natural or synthetic and the sample can be any type of sample suitable for analysis, such as, but not limited to, a biological sample. Non-limiting examples of the sample comprising the analyte, include but are not limited to cells or tissues and cultures (or subcultures) thereof, crude or processed cell lysates (including whole cell lysates), body fluids, tissue extracts or cell extracts. Still other non-limiting examples of samples include but are not limited to fractions from a separations process such as a chromatographic separation or an electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more analytes that are peptides formed by treatment of the total protein component of a crude cell lysate with a proteolytic enzyme to thereby digest precursor protein or proteins.

According to various embodiments, samples containing one or more analytes having at least one carboxyl or phenolic functional group may be enriched by various methods prior to analysis. Exemplary enrichment methods can comprise, without limitation, protein precipitation, liquid-liquid extraction, solid-liquid extraction, affinity capture/release, antibody mediated enrichment and ultrafiltration. Other enrichment methods, or a combination of two or more enrichment methods may be used.

As noted above, in various embodiments, methods provided herein can comprise analyzing (e.g., detecting, quantifying) the derivatized analyte(s). As will be appreciated by a person skilled in the art in light of the present teaching, a variety of analytical methods can be used to analyze the derivatized analyte including mass spectrometry or UV/VIS spectroscopy, by way of non-limiting example.

In some example embodiments, the analyzing step comprises detecting one of more mass signals associated with any of said derivatized analytes and one or more fragments thereof. The detection of mass signals can be used with any standard mass spectrometer, such as, but not limited to, a QTRAP® 5500 mass spectrometer. Generally, the specific mass spectrometer and mode of operation is not critical, though the teachings herein may be particularly beneficial in enabling ionization of the derivatized analytes using an ion source operating in positive ion mode. Though many carboxyl and phenolic functional group containing compounds have previously been difficult to analyze using positive-mode mass spectrometry techniques, derivatization methods in accordance with the present teachings may substantially improve the ionization efficiency in positive ion mode.

In some embodiments, the method comprises quantitating the amount of the carboxyl or phenolic-containing analyte(s) in the sample. The quantitating can be done, for example, by comparing the mass spectra to a standard. The standard can be an internal standard or an analyte standard. For example, heavy atom labeled analytes can be used. The heavy atom labeled analytes can be heavy atom derivatized carboxyl or phenolic-containing analyte, such as those described herein.

Figure 5:
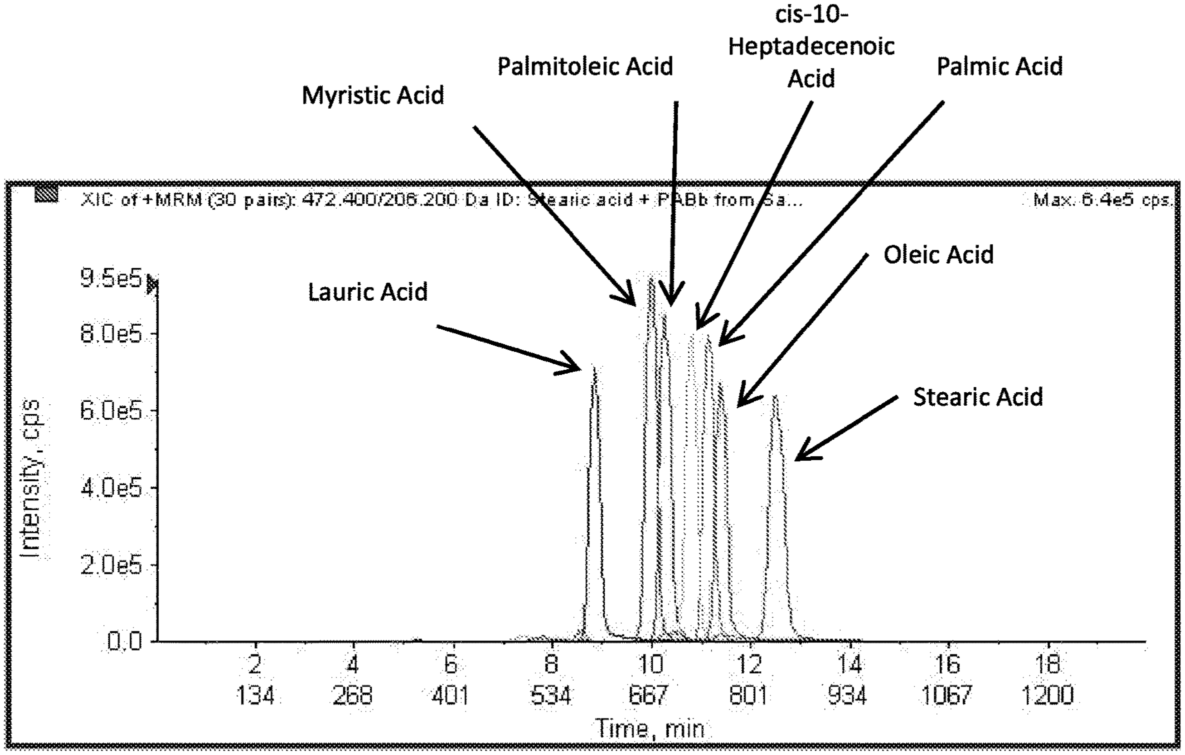
FIG. 5 depicts an example chromatogram of a panel of steroids derivatized with the PAB-based derivatizing agent shown in FIG. 2A.

FIG. 5 depicts the LC/MS/MS chromatogram of a panel of fatty acids derivatized with a substituted PAB compound of Formula III. The panel consisted of lauric acid, myristic acid, palmitoleic acid, cis-10-heptadecenoic acid, palmic acid, oleic acid, and stearic acid. A solution of 10 μM of each of these fatty acids was reacted with the PAB-based of Formula III in 0.75 M triethanolamine in acetonitrile and heated at 60° C. for 1 h. The reaction mixture was injected into a LC/MS-MS (SCIEX 3200 QTRAP with a Turbo Spray source and an Agilent 1200 LC) and separated using a $C_{13}$ column. The figure shows the extracted ion chromatogram using the MRM transitions for the derivatized fatty acids (lauric acid 388.3/206.2, myristic acid 416.3/206.2, palmitoleic acid 442.3/206.2, cis-10-heptadecenoic acid 456.3/206.2, palmic acid 444.3/206.2, oleic acid 470.4/206.2, and stearic acid 472.4/206.2).

Figure 6A:
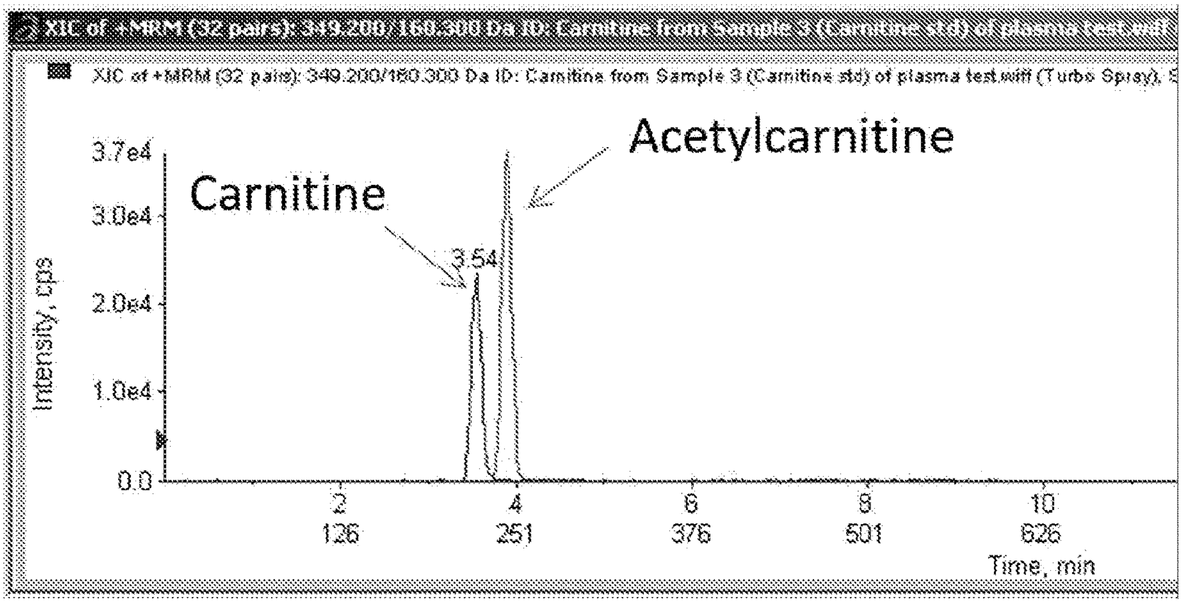
FIG. 6A depicts an example chromatogram of a plasma sample preparation derivatized with the PAB-based derivatizing agent shown in FIG. 2A. The XIC for carnitine and acetylcarnitine is shown.

FIG. 6A depicts the LC/$MS^2$ chromatogram of a standard of L-carnitine and acetyl-L-carnitine derivatized with a PAB-based derivatizing agent in accordance with the present teachings. A solution of carnitine and acetylcarnitine was reacted with the PAB-based of Formula III in 0.75 M triethanolamine in acetonitrile and heated at 60° C. for 1 h. The reaction mixture was injected into a LC/MS-MS (SCIEX 3200 QTRAP with a Turbo Spray source and an Agilent 1200 LC) and separated using a C13 column. The figure shows the extracted ion chromatogram using the MRM transitions for the derivatized carnitine (349.2/160.3) and acetylcarnitine (391.2/160.3).

Figure 6B:
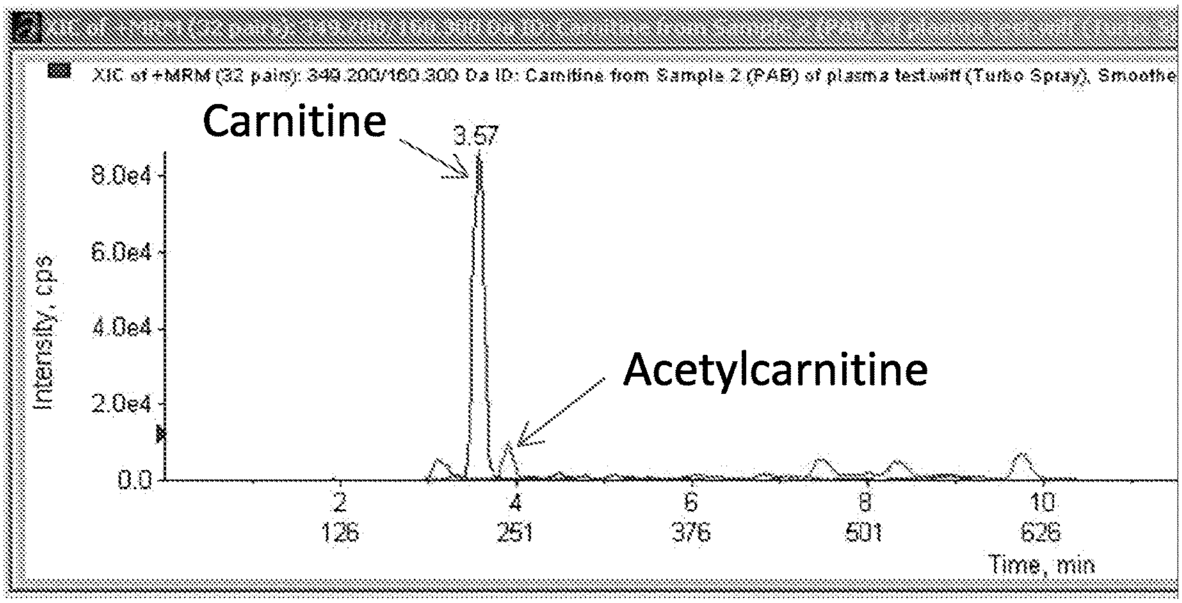
FIG. 6B depicts an example chromatogram of a standard mixture of carnitine and acetylcarnitine derivatized with the PAB-based derivatizing agent shown in FIG. 2A.

FIG. 6B depicts the LC/$MS^2$ chromatogram for a plasma sample in which carboxyl-containing analytes were derivatized with a PAB-based derivatizing agent of Formula III. In particular, 200 μL of acetonitrile was added to 50 μL of a plasma sample to precipitate proteins in the sample and the sample was spun to pellet the proteins. 50 μL of supernatant was removed and dried. The dried supernatant was reconstituted in 20 μL of 0.75 M triethanolamine in acetonitrile, which was then mixed with 20 μL of the PAB-based derivatizing agent of Formula III in acetonitrile (20 mg/mL) and heated at 60° C. for 1 hour. 60 μL of 2% formic acid in water was then added and 2 μL was injected into a LC/MS-MS (SCIEX 3200 QTRAP with a Turbo Spray source and an Agilent 1200 LC) and separated using a C13 column. The figure shows the extracted ion chromatogram using the MRM transitions for the derivatized carnitine (349.2/160.3) and acetylcarnitine (391.2/160.3).

In accordance with various aspects of the present teachings, methods of synthesizing various PAB-based derivatizing agents are provided herein and which may include reacting a substituted or non-substituted PAB with one or more additional compounds such as an aminooxy reagent to form the PAB-based derivatizing agent. For example, in some aspects, PAB-based derivatizing agents in accordance with various aspects of the present teachings may be produced by reacting a substituted or non-substituted PAB with an aminooxy compound having a quaternary amine or a substituent thereof (including heavy atom derivatives of the aminooxy compounds). Examples of such aminooxy compounds may have the following structure:

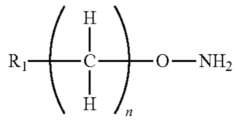

wherein n is from 1 to 20, from 1 to 15, from 1 to 10, from 1 to 5, or from 2 to 4 and $R_1$ is a quaternary amine or a substituent having the structure:

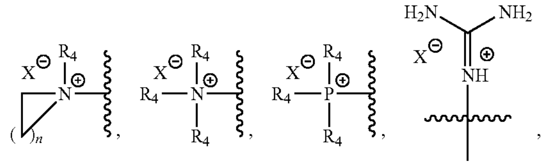

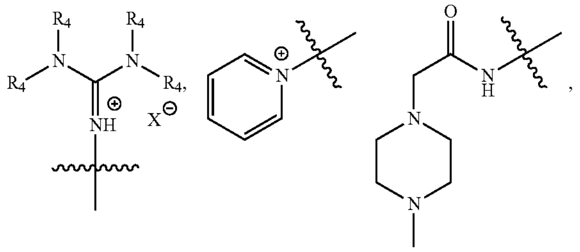

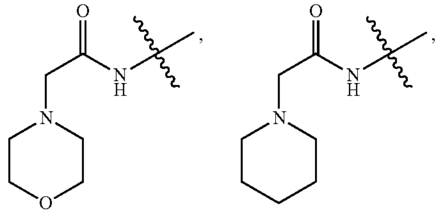

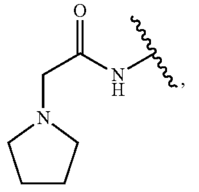

or

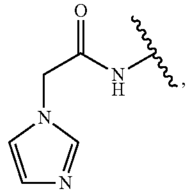

wherein each $R_4$ is independently H or a cyclic, branched or straight chain $C_1$-$C_{18}$ alkyl, $C_1$-$C_{18}$ alkene, or $C_1$-$C_{18}$ alkyne, and wherein m is an integer between 1 and 20, and X is an anion.

Particular examples of such aminooxy compounds include $H_2NO—(CH_2)_n—(NR_3)^+$ (or a heavy atom derivative thereof), where n is 1 to 20, and each R is independently hydrogen or a cyclic, branched or straight chain $C_1$-$C_{18}$ alkyl, $C_1$-$C_{18}$ alkene, or $C_1$-$C_{18}$ alkyne. The compound $H_2NO—(CH_2)_3—(NH_3)^+$ is one example of such an aminooxy reagent.

Figure 7A:
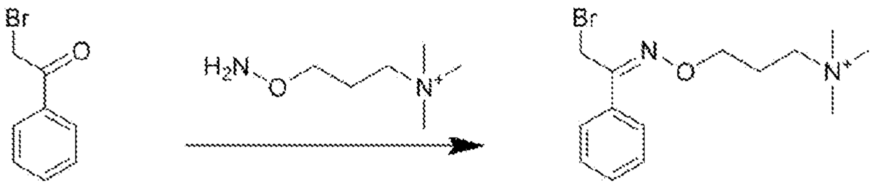
FIGS. 7A-C depicts the synthesis of example PAB-based derivatizing agents in accordance with various aspects of the applicant's teachings.
Figure 7B:
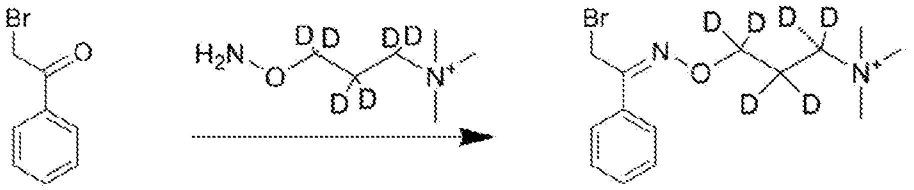
Figure 7C:
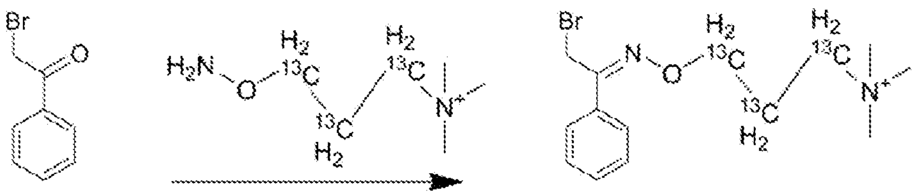

With reference to FIG. 7A, a non-substituted PAB compound of Formula I (obtained from Sigma Aldrich, CAS 70-11-1) was reacted with 5 equivalents of aminooxy compound $H_2NO—(CH_2)_3—(NH_3)^+$ (Amplifex Keto Reagent) in 5% acetic acid/methanol and stirred at ambient temperature for 12 h to form the PAB-based derivatizing agent of Formula VI. The product was purified by $C_{18}$ flash chromatography. In addition, as noted above, heavy atom derivatives the various compounds described herein can additionally be employed, for example, by incorporating one or more of deuterium atoms ($^2H$ or D), $^{13}C$, $^{17}O$, $^{18}O$, and $^{15}N$, by way of non-limiting example. For example, FIG. 7B depicts the reaction of PAB of Formula I with a heavy atom derivative $H_2NO—(CD_2)_3$-$(NH_3)^+$, while FIG. 7C depicts the reaction with the heavy atom derivative $H_2NO—(^{13}CH_2)_3—(NH_3)^+$.

Figure 8A:
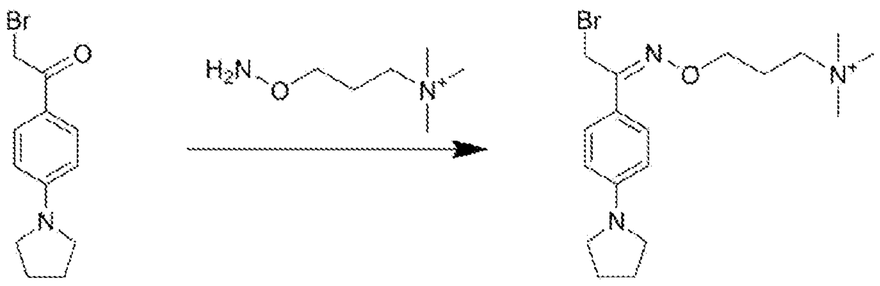
FIGS. 8A-C depicts the synthesis of other example PAB-based derivatizing agents in accordance with various aspects of the applicant's teachings.
Figure 8B:
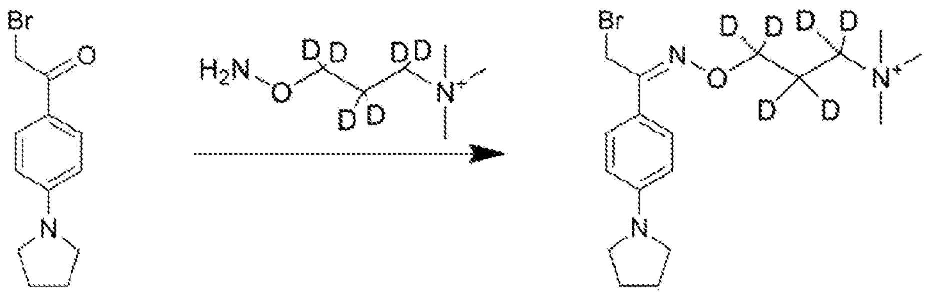
Figure 8C:
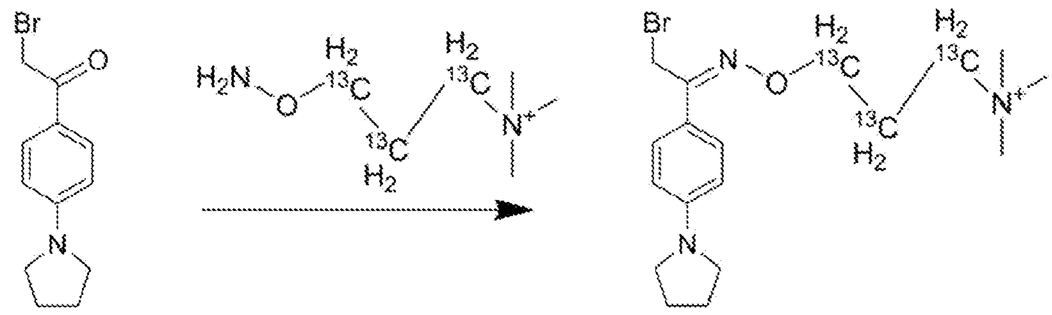

With reference to FIG. 8A, a substituted PAB compound of Formula III (2-Bromo-4'-(1-pyrrolidinyl)acetophenone obtained from Alfa Aesar, CAS No. 216144-18-2) was reacted with 5 equivalents of aminooxy compound $H_2NO—(CH_2)_3—(NH_3)^+$ (Amplifex Keto Reagent) in 5% acetic acid/methanol and stirred at ambient temperature for 12 h to form the PAB-based derivatizing agent of Formula VII. The product was purified by $C_{18}$ flash chromatography. FIG. 8B depicts the reaction of PAB of Formula III with a heavy atom derivative $H_2NO—(CD_2)_3$-$(NH_3)^+$, while FIG. 8C depicts the reaction with the heavy atom derivative $H_2NO—(^{13}CH_2)_3—(NH_3)^+$.

Figure 9:
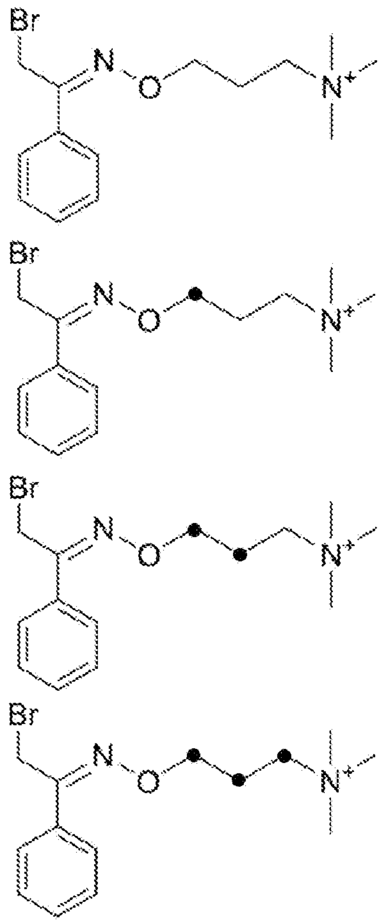
FIG. 9 depicts an exemplary set of four PAB-based derivatizing agents in accordance with various aspects of the applicant's teachings.

According to some embodiments, one or more heavy atom derivatives of PAB-based derivatizing agents can be used as an internal standard in one or more sample runs. Additionally or alternatively, one or more of a PAB-based derivatizing agent and heavy atom derivatives thereof may be used as a set, for example, in relative or absolute quantitation in multiplex assays. For example, sets of various heavy atom derivatives of PAB-based derivatizing agents can be used for two-plex, three-plex, four-plex, and other multi-plex assays. By way of non-limiting example, FIG. 9 depicts an exemplary set of four PAB-based derivatizing agents of Formula VI that can be used in a four-plex assay according to various embodiments of the present teachings. As shown, each of the depicted PAB-based derivatizing agent comprises a non-substituted PAB compound of Formula I that has been reacted with a different heavy isotopic version of the aminooxy compound $H_2NO—(CH_2)_3—(NH_3)^+$.

According to some embodiments, kits are also provided. In some embodiments, the kit comprises a PAB-based derivatizing reagent, such as but not limited to those described herein. In some embodiments, the PAB-based derivatizing agent is a compound of Formula II or a heavy atom derivative thereof. According to various embodiments, the kit can comprise buffers, one or more chromatographic columns, and optionally other reagents and/or components useful in carrying out the methods or assay. In some embodiments, the kit can comprise, for example, a homogeneous assay such that the user need only add a sample. In some embodiments, the kit can comprise calibration or normalization reagents or standards. Information pertaining to instrument settings that can or should be used to perform an assay can also be included in the kit. In some embodiments, information pertaining to sample preparation, operating conditions, volumetric amounts, temperature settings, and the like, can be included with the kit. The kit can also be packaged in a hermetically sealed container containing one or more reagent vessels and appropriate instructions. An electronic medium can be included in the kit, having stored thereon electronic information pertaining to one or more assays, measurement values, transition pairs, operating instructions, software for carrying out operations, a combination thereof, or the like. According to various embodiments, a method can be provided for the synthesis of the PAB-based derivatizing reagent and its intermediates. In some embodiments, the kit can comprise at least one standard comprising a known concentration of a known phenol or carboxyl-containing analyte (e.g., an analyte of interest). According to some embodiments, kit can comprise instructions for derivatizing, quantifying, and detecting the phenol or carboxyl-containing analyte.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

What is claimed is:

1. A method of analyzing a sample, comprising:

reacting a sample containing or suspected of containing one or more analytes having at least one of a carboxyl and a phenolic functional group with a derivatizing agent to produce one or more derivatized analytes, and analyzing the one or more derivatized analytes;

wherein the derivatizing agent comprises a substituted PAB of the formula:

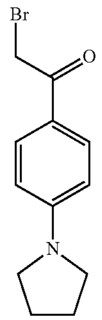

or a heavy atom derivative thereof.

2. The method of claim 1, wherein the sample contains or is suspected of containing one or more analytes having at least one carboxyl functional group.

3. The method of claim 2, wherein the one or more analytes having at least one carboxyl functional group comprise one or more of fatty acids, bile acids, amino acids, and carnitines.

4. The method of claim 2, wherein the one or more analytes having at least one carboxyl functional group comprises at least one eicosanoid.

5. The method of claim 4, wherein the at least one eicosanoid comprises one or more of prostaglandin, thromboxane, EpETE, HETE, HODE, and HpETE.

6. The method of claim 1, wherein the sample contains or is suspected of containing one or more analytes having at least one phenolic functional group.

7. The method of claim 6, wherein the one or more analytes having at least one phenolic functional group comprise at least one hormone.

8. The method of claim 7, wherein the at least one hormone comprises one or more estrogens, and optionally wherein the one or more estrogens is selected from the group consisting of estrone, estradiol, and estriol.

9. The method of claim 1, wherein the sample is a biological sample, and optionally wherein the biological sample is selected from blood, plasma, serum, urine, saliva, cerebral fluid, tissue, hair, or body fluids.

10. The method of claim 1, wherein analyzing the derivatized analytes is performed by a mass spectrometer, and optionally wherein the derivatized analytes are ionized in positive ion mode prior to using the mass spectrometer.

* * * * *